(12) United States Patent
Shum et al.

(10) Patent No.: US 10,851,136 B2
(45) Date of Patent: Dec. 1, 2020

(54) RECOMBINANT LACTIC ACID BACTERIA AND THE USE THEREOF IN ORAL UNIVERSAL INFLUENZA VACCINE

(71) Applicant: CREATION PLUS BIOTECHNOLOGY CO. LTD, Hong Kong (HK)

(72) Inventors: Chung Yan Shum, Hong Kong (HK); Tak Keung Andy Wong, Hong Kong (HK)

(73) Assignee: CREATION PLUS BIOTECHNOLOGY CO. LTD, Hong Kong (HK)

( * ) Notice: Subject to any disclaimer, the term of this patent is extended or adjusted under 35 U.S.C. 154(b) by 23 days.

(21) Appl. No.: 15/777,672

(22) PCT Filed: Nov. 21, 2016

(86) PCT No.: PCT/CN2016/106690
§ 371 (c)(1),
(2) Date: May 21, 2018

(87) PCT Pub. No.: WO2017/084635
PCT Pub. Date: May 26, 2017

(65) Prior Publication Data
US 2018/0334481 A1    Nov. 22, 2018

Related U.S. Application Data

(60) Provisional application No. 62/257,242, filed on Nov. 19, 2015.

(51) Int. Cl.
| | | |
|---|---|---|
| *C07K 14/005* | (2006.01) |
| *C07K 14/205* | (2006.01) |
| *A61K 39/12* | (2006.01) |
| *C07K 14/285* | (2006.01) |
| *A61K 39/145* | (2006.01) |
| *C07K 14/435* | (2006.01) |
| *A61K 39/00* | (2006.01) |

(52) U.S. Cl.
CPC ............ *C07K 14/005* (2013.01); *A61K 39/12* (2013.01); *A61K 39/145* (2013.01); *C07K 14/205* (2013.01); *C07K 14/285* (2013.01); *C07K 14/43504* (2013.01); *A61K 2039/523* (2013.01); *A61K 2039/542* (2013.01); *A61K 2039/545* (2013.01); *C12N 2760/16134* (2013.01)

(58) Field of Classification Search
None
See application file for complete search history.

(56) References Cited

FOREIGN PATENT DOCUMENTS

WO    WO-2015164674 A1 * 10/2015

OTHER PUBLICATIONS

Mallajosyula et al. PNAS Jun. 24, 2014 111 (25) E2514-E2523.*

* cited by examiner

*Primary Examiner* — Oluwatosin A Ogunbiyi
(74) *Attorney, Agent, or Firm* — Idea Intellectual Limited; Margaret A. Burke; Sam T. Yip

(57) ABSTRACT

The present invention relates to an oral universal influenza vaccine comprising recombinant lactic acid bacteria which express proteins including but not limited to ferritin protein plus highly-conserved stem fragment of hemagglutinin (HA) proteins expressed in all known influenza viruses. The present invention also relates to the recombinant protein comprising the highly-conserved stem fragment of HA and ferritin proteins.

17 Claims, 7 Drawing Sheets
Specification includes a Sequence Listing.

FIG. 1 (SEQ ID NO: 1)

RECOMBINANT LACTIC ACID BACTERIA AND THE USE THEREOF IN ORAL UNIVERSAL INFLUENZA VACCINE

CROSS-REFERENCE TO RELATED APPLICATIONS

This application claims priority from the U.S. provisional patent application Ser. No. 62/257,242 filed Nov. 19, 2015, and the disclosure of which is incorporated herein by reference in its entirety

TECHNICAL FIELD

The present invention relates to a recombinant lactic acid bacteria and the use thereof in an oral universal influenza vaccine. In particular, the present invention relates to a recombinant lactic acid bacteria expressing highly-conserved stem-fragment of hemagglutinin (HA) proteins which are expressed in all known Influenza viruses, and the use thereof in an oral formulation of a universal influenza vaccine.

BACKGROUND OF THE INVENTION

Global out-breaks of influenza virus continuous to cause a considerable morbidity and mortality. According to the Centers of Disease Control and Prevention (CDC), seasonal influenza leads to over 200,000 hospitalization and 36,000 deaths each year worldwide. In addition, the death rate and the associated economic costs in poultries are enormously as all poultries in the same farm and in close vicinity are terminated if one bird was tested positive. Currently, the best strategy to prevent influenza infection is through vaccination. Given the fact that there are many influenza viruses and their antigenic structures, especially the head domain region, are always changing, the seasonal vaccine components must be frequently updated and modified in order to provide protection against continuous emerging viral strains. The currently available influenza vaccines are not universal which target the head domain of hemagglutinin (HA) on the surface of influenza viruses. It is well known that the globular head domains of hemagglutinin (HA) of influenza virus are highly variable with a high mutation rate. This obviously limits the therapeutic effectiveness of the currently used head-directed influenza vaccines against variant, mutated and drifted variants influenza viruses.

The head domain region is so variable from year to year and that is why new vaccines are needed in order to keep up with the ever changing virus strains every season. Determining the likelihood that a particular influenza vaccine chosen would protect a person from influenza-related illness, the similarity between the influenza viruses and the influenza vaccine designed to protect against is crucial. The development of the traditional influenza vaccine currently used includes the prediction of which viruses should be included in the development of injectable vaccine requires many months in advance in order for vaccine to be produced and delivered on time to deal with constantly mutating influenza viruses (known as drift) every year. Every year, the World Health Organization (WHO) predicts which strains of the influenza virus are most likely to be circulating in the next year allowing pharmaceutical companies to develop vaccines that will provide the best immunity and protection against these strains. The vaccine is reformulated each season for a few specific flu strains but does not include all strains active in the world during the current season and the following seasons and years. It takes about six months for the manufacturers to formulate and produce the millions doses required to deal with the seasonal epidemic. Occasionally, a new or overlooked strain becomes prominent during that season. When the influenza vaccine developed failed to match the circulating viruses, it is possible that no benefit and protection from influenza vaccine injected could occur. It is also possible to get infected just before vaccination and became sick because the administered vaccine in general takes about two weeks to become effective. If the virus changes itself and is able to infect people and spread, an influenza pandemic—a world outbreak of the disease—could begin. No one can predict for sure when an influenza pandemic strikes. A continuous search and modification of "NEW" vaccine for injection by drug companies is needed for the coming influenza pandemic every year. However, prediction and estimation of type(s) of influenza pandemic are obviously not reliable and the process is tedious in view of the expected continuous mutation of the structure of hemagglutinin and type(s) of influenza involved. A wrong prediction can result in a great loss of enormous amount of money and human lives. Most importantly, a wrong prediction of the administered vaccine cannot provide proper protection for humans, poultries and other livestock against influenza infection.

Current influenza vaccination in poultries and human utilizes injectable form (liquid) of dead/inactivated antigen usually via intra-muscular route. Despite the fact that this is the most common route of administration, the procedures require trained personnel (i.e. nurses, doctors, trained farmers) to carry out vaccination procedures. Missed dose occasionally occurs which obviously curtails the overall effectiveness of the influenza vaccination. Also, the traditional vaccination of poultries is labor-intensive and very tedious to work with. On the other hand, the traditional influenza vaccines in liquid form required to be refrigerated at 2-8° C. which is obviously a disadvantage in some areas i.e. hot deserts in Sub-Sahara African and poor rural areas in China where a shortage of electricity as well as poor transportation are common problems. Besides, current vaccines are attenuated pathogenic microorganism which carries the risk that immune reactions triggered against the carrier itself and reduce the efficacy of the booster vaccine. In addition, vaccine in liquid form contains preservatives which some people believe that these preservatives pose health hazards which are related to neurological disorders after vaccine injections. For instance, Autism children are suspected to be related to use of the liquid-form vaccines with the presence of preservatives. Last but not least, the shelf-life of the liquid-form vaccine is rather short i.e. usually less than 3 months which obviously is a disadvantage.

Comparatively, the stem domains of hemagglutinin (HA) are highly conserved across divergent groups of influenza virus strains known (FIG. 6). Therefore, they can trigger the production of broadly neutralizing antibodies and confer the heterologous protections against divergent groups of influenza virus strains.

Ferritin is a globular protein complex consisting of 24 protein subunits and is the primary intracellular iron-storage protein in both prokaryotes and eukaryotes, keeping iron in a soluble and non-toxic form. The protein is produced by almost all living organisms, including algae, bacteria, higher plants, and animals. Ferritin is found in most tissues as a cytosolic protein, but small amounts are secreted into the serum where it functions as an iron carrier. It has been reported that the introduction of ferritin to antigen could enhance the antigenicity of the antigen involved. This would elicit a broader and more potent immunity than the traditional influenza vaccines.

There exists a need for a pharmaceutically acceptable carrier of influenza vaccines that contain these highly-conserved stem domains of HA proteins coupled to ferritin proteins. Lactic acid bacteria (LAB) are one of the most suitable candidates including *Lactobacillus* sp. because they are Generally Regarded As Safe (GRAS) which can be non-pathogenic carriers for oral vaccine. Techniques of transforming LAB are well developed and a variety of plasmids is available in the market for controlling and modulating the expression of the desired proteins. Preservation and storage of the transformed LAB are also safe and convenient. They are considered as harmless to humans and animals including livestock with a good record of safe uses as food products. Lactic acid bacteria, especially *Lactobacillus casei*, are food grade microorganisms and are safe for human and animals consumption.

SUMMARY OF THE INVENTION

Accordingly, a first aspect of the present invention relates to a recombinant lactic acid bacteria transformed with an expression vector that contains a DNA sequence encoding the highly-conserved stem domains of influenza hemagglutinin, the ferritin protein, and other regions. Said other regions may include but not limited to an orange fluorescent protein (OFP) which enhances the immunogenicity, a linker between the OFP and the highly-conserved stem domains of influenza hemagglutinin (HA), and a linker between the highly-conserved stem domains of influenza HA and the ferritin protein. In an exemplary embodiment, the encoding sequences of OFP and stem domains of influenza HA are modified to enhance the immunogenicity of the expressed protein against human and other animals and/or expression efficiency in the host cells after transformation. The expressed proteins of OFP, the stem domains of influenza HA, and the ferritin protein from said DNA sequence are therefore linked by said corresponding linker.

The present modified encoding sequences of the OFP and stem domains of influenza HA are preferably for *Lactobacillus* strains including but not limited to *Lactobacillus casei*, *Lactobacillus acidophilus*, and *Lactobacillus plantarum*. It is also suitable for other LAB such as *Lactococcus*, e.g., *Lactococcus lactis*.

The expression vector that can be used in the present invention is preferably an expression vector for gram-positive host, which includes but not limited to pTRKH3 vector, pMSP3535, pDL378 and other kinds of gram-positive expression vectors. In a preferred embodiment, pTRKH3 vector is used.

The influenza that the present recombinant LAB can cause immunogenicity in a human or other animals includes but not limited to H1, H3, and H5 subtypes, since the modified stem domains of influenza HA expressed in the present recombinant LAB are highly conserved in influenza viruses, which could elicit broadly neutralizing antibodies against a wide variety of influenza strains.

The present recombinant LAB can be formulated into different pharmaceutically acceptable forms including but not limited to powder, pills, capsules, liquid, and tablets. In a preferred embodiment, the present recombinant LAB is administered orally to a subject which is human or other animals. However, other administration route which may cause immuno-rejection to the present recombinant LAB should be avoided, e.g., direct injection of the LAB in general subcutaneously or intravenously is known to cause allergic reaction in the recipient.

A second aspect of the present invention relates to a recombinant protein expressed from the DNA sequence encoding the highly-conserved stem domains of influenza hemagglutinin, the ferritin protein, and other regions of the first aspect of the present invention and isolated from the transformed host cells. It should be understood that any conventional method which can be used in transforming an expression vector into a gram-positive host cell such as electroporation can be employed. It should be understood that the highly-conserved stem domains of influenza hemagglutinin expressed from the DNA sequence of the present invention has the ability to induce antibody in the recipient even in the absence of the ferritin protein and other regions of the recombinant protein. In other words, the recombinant protein of the present invention can be the highly-conserved stem domains of the influenza hemagglutinin alone.

A third aspect of the present invention relates to a use of the recombinant lactic acid bacteria according to the first aspect of the present invention or the recombinant protein according to the second aspect of the present invention in the manufacture of a medicament, e.g., a vaccine, for the treatment of influenza by inducing antibody in a subject against a variety of influenza viruses. The medicament according to the third aspect of the present invention is preferably an oral formulation comprising the recombinant lactic acid bacteria or the recombinant protein. The oral formulation comprising the recombinant protein of the present invention further comprises a pharmaceutically acceptable carrier such as a capsule, tablet, salt, buffer, ester, etc. The oral formulation comprising the recombinant lactic acid bacteria of the present invention is in powder form, pills, capsules, tablets, liquid, or buffer, etc. The influenza viruses which the antibody induced by the recombinant lactic acid bacteria or the recombinant protein can target and bind to comprise H1, H3 and H5 subtypes, and other H subtypes of influenza viruses. In a preferred embodiment, the oral formulation comprising an effective amount of the recombinant lactic acid bacteria of the present invention is administered to a subject in needs thereof. Said subject includes human and other animals. When the subject is a small animal such as mouse, the effective amount of the recombinant lactic acid bacteria in said oral formulation is about $1 \times 10^9$ cfu and the oral formulation is administered once daily for three consecutive days on a weekly basis and for two consecutive weeks.

These and other examples and features of the present invention and methods will be set forth in part in the following Detailed Description. This Summary is intended to provide an overview of the present invention, and is not intended to provide an exclusive or exhaustive explanation. The Detailed Description below is included to provide further information about the present disclosures and methods.

BRIEF DESCRIPTION OF THE DRAWINGS

FIG. 1 is a schematic diagram depicting the design of the DNA insert into an expression vector for transformation into a *Lactobacillus* strain according to a preferred embodiment of the present invention: Region 1 represents a modified DNA sequence of orange fluorescent protein (OFP); Region 2 represents a modified DNA sequence of influenza HA stem fragment; Region 3 represents a DNA sequence of ferritin; two small brackets represent two linkers for linking up the DNA sequences of the OFP and influenza HA stem fragment and those of the influenza HA stem fragment and the ferritin, respectively.

DETAILED DESCRIPTION OF THE INVENTION

Figure 2:
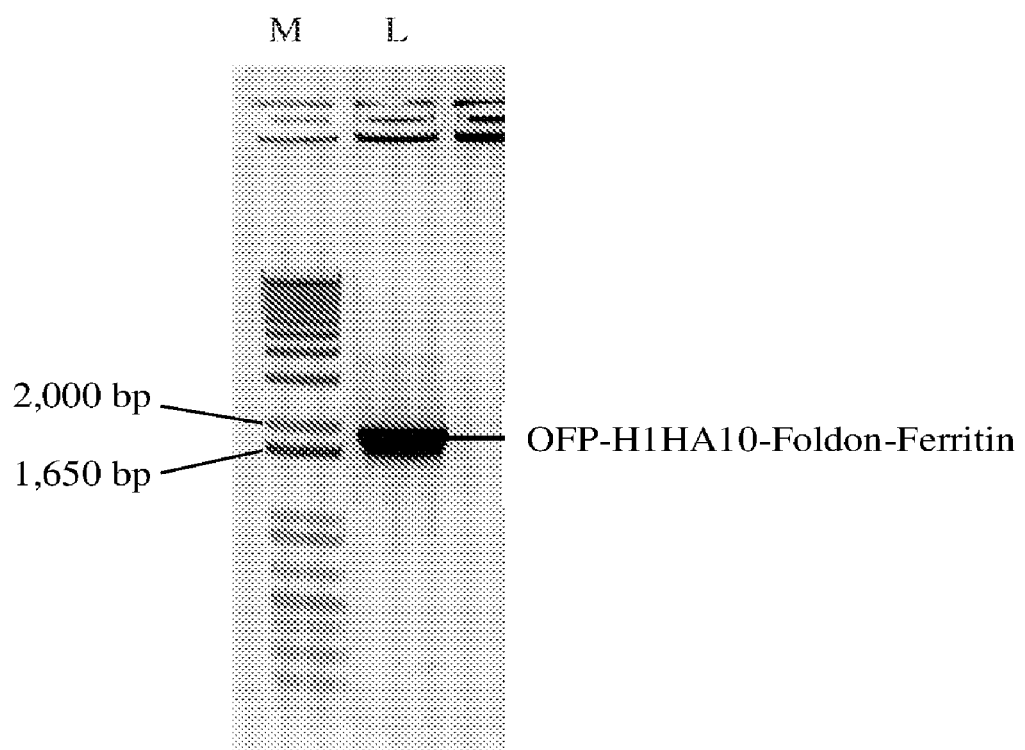
FIG. 2 shows the result of an agarose gel analysis of *Lactobacillus casei* transformed clones with an expression vector containing the DNA insert depicted in FIG. 1: (M) DNA marker: (L) PCR amplification from transformed *Lactobacillus casei* clone for clone confirmation.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

As described herein, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

Definitions

The singular forms "a,", "an" and "the" can include plural referents unless the context clearly dictates otherwise.

The term "about" can allow for a degree of variability in a value or range, for example, within 10%, or within 5% of a stated value or of a stated limit of a range.

The term "independently selected from" refers to referenced groups being the same, different, or a mixture thereof, unless the context clearly indicates otherwise. Thus, under this definition, the phrase "X1, X2, and X3 are independently selected from noble gases" would include the scenario where, for example, X1, X2, and X3 are all the same, where X1, X2, and X3 are all different, where X1 and X2 are the same but X3 is different, and other analogous permutations.

DETAILED DESCRIPTION OF PREFERRED EMBODIMENTS

The present invention is not to be limited in scope by any of the following descriptions. The following examples or embodiments are presented for exemplification only.

EXAMPLES

The embodiments of the present invention can be better understood by reference to the following examples which are offered by way of illustration. The present invention is not limited to the examples given herein.

Figure 1:
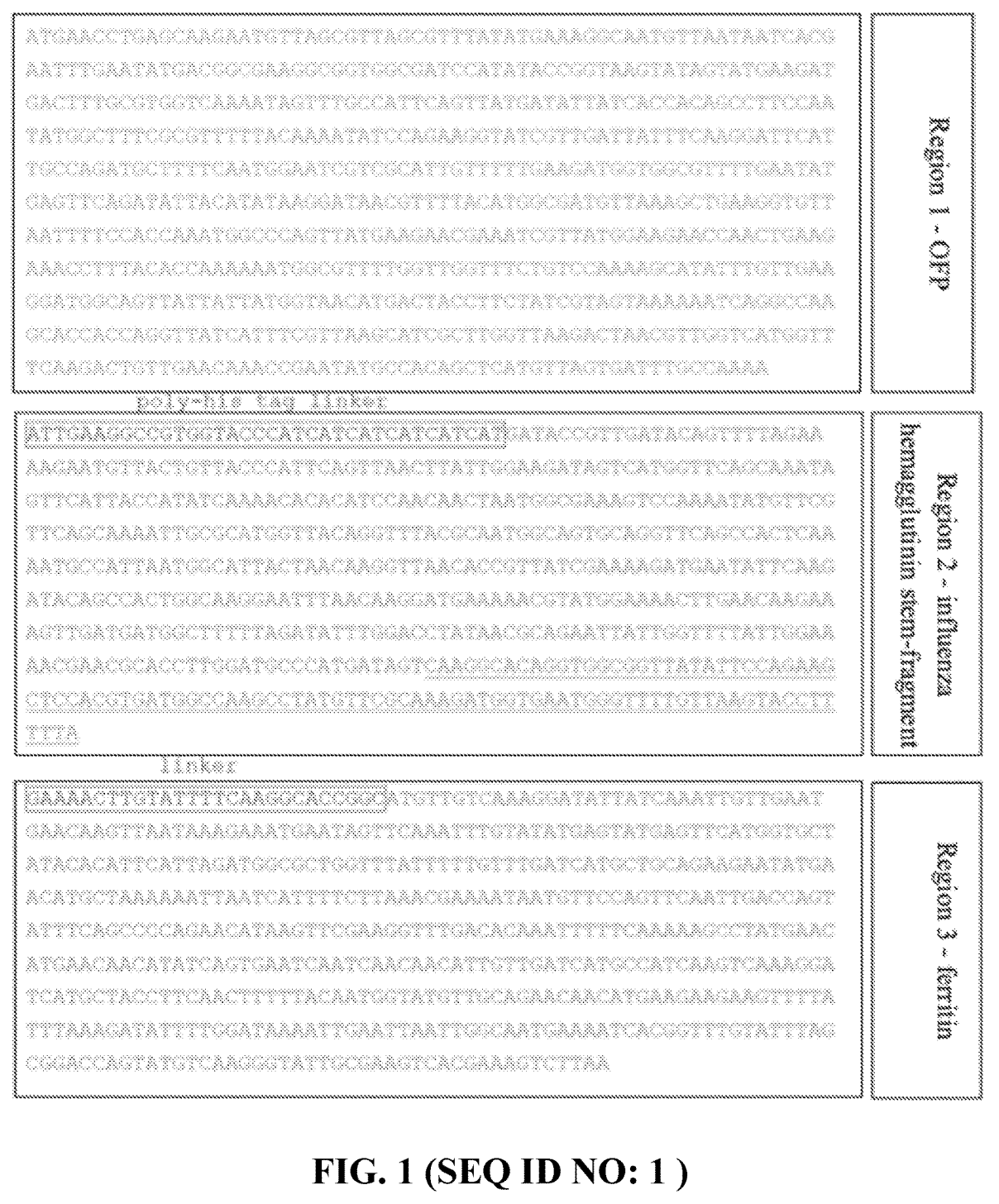

Example 1—Design of DNA Insert and Transformation of Expression Vector Containing the Same in Host Cell FIG. 1 shows the design of DNA insert comprising a modified orange fluorescent protein (OFP) encoding sequence (Region 1). The sequence is originated from *Cerianthus* sp. (GenBank sequence database: AAP55761.1). The protein expressed from this modified OFP encoding sequence can enhance the immunogenicity of the recombinant protein of the present invention in the recipient. The modified encoding sequence of OFP also matches the codon preference of LAB in general. However, other commercially available fluorescent protein having the foregoing characteristics can also be used in the DNA insert.

The DNA insert of FIG. 1 also comprises a modified influenza hernagglutinin stem fragment encoding sequence (Region 2), which is referenced to protein sequences disclosed in Mallajosyula et al. (Mallajosyula, Vamsee V A. et al. *Proceedings of the National Academy of Sciences* 111.25 (2014): E2514-E2523). Differing from the disclosed sequences in Mallajosyula et al., reverse translation from one of the disclosed sequences followed by codon optimization to *Lactobacillus caseiare* done, and some modifications are madein the DNA sequence after reverse translation for optimization purposes. A T4 bacteriophage fibritin foldon is also encoded in the underlined sequence in Region 2 as shown in FIG. 1.

The DNA insert of FIG. 1 further comprises an encoding sequence of ferritin protein (Region 3), which is originated from *Helicobacter pylori* (NCBI Reference Sequence Database: WP_000949190.1).

Between Region 1 and Region 2, the DNA insert of FIG. 1 also comprises a first linker which is a poly-His tag linker. The first linker comprises an Xa protease encoding sequence and a restriction site of KpnI, before the poly-His encoding sequence.

Between Region 2 and Region 3, the DNA insert of FIG. 1 further comprises a second linker. The second linker comprises TEV protease encoding sequence and a restriction site of AgeI.

The sequence of the DNA insert of FIG. 1 is also represented by SEQ ID NO: 1. Optionally, a sequence comprising at least one restriction site can be inserted before and/or after the start codon and stop codon of the DNA insert. For example, NcoI and NdeI restriction sites can be inserted before the start codon; BamHI restriction site can be inserted after stop codon.

Figure 7:
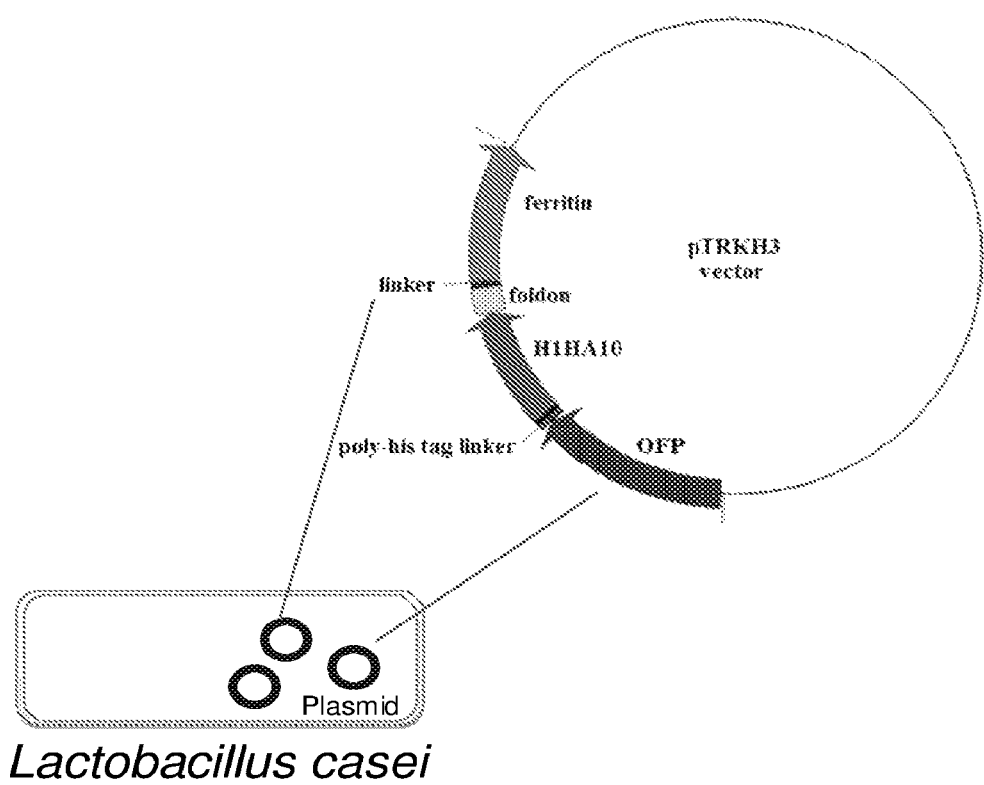
FIG. 7 shows the plasmid construction of the expression vector with the desired DNA insert for transformation into *Lactobacillus casei* according to a preferred embodiment of the present invention.

The DNA sequence as shown in FIG. 1 (or SEQ ID NO: 1) is cloned in the pTRKH3 expression vector for protein expression in the transformed *Lactobacillus casei*. FIG. 7 shows the plasmid construction map of said pTRKH3 expression vector inserted with the DNA encoding sequence of SEQ ID NO: 1.

It should be understood that the order of different regions in the DNA insert as described in the present invention can be changed, provided that the expressed proteins from the *Lactobacillus casei* transformed with said expression vector with these different DNA inserts having different combinations of said regions are capable of inducing antibody against the variety of H subtype influenza viruses in the subject that receives the formulation comprising the transformed *Lactobacillus casei*. For example, these different inserts may have the following combinations of different regions:

(i) Region 1 (OFP) is followed by Region 3 (ferritin protein) and then Region 2 (stem domain of influenza HA), which encoding sequence is represented by SEQ ID NO: 2;
(ii) Region 2 (stem domain of influenza HA) is followed by Region 1 (OFP) and then Region 3 (ferritin protein), which encoding sequence is represented by SEQ ID NO: 3;
(iii) Region 2 (stem domain of influenza HA) is followed by Region 3 (ferritin protein) and then Region 1 (OFP), which encoding sequence is represented by SEQ ID NO: 4;
(iv) Region 3 (ferritin protein) is followed by Region 1 (OFP) and then Region 2 (stem domain of influenza HA), which encoding sequence is represented by SEQ ID NO: 5;
(v) Region 3 (ferritin protein) is followed by Region 2 (stem domain of influenza HA) and then Region 1 (OFP), which encoding sequence is represented by SEQ ID No: 6.

It is also possible to only include the encoding sequence of Region 2 into the expression vector, from which the protein expressed can still induce antibody against said variety of H subtype influenza viruses in said subject.

To confirm positive clones. PCR amplification is employed to screen and identify *Lactobacillus casei* successfully transformed with pTRKH3 expression vector containing the DNA insert of SEQ ID NO: 1, namely OFP-H1HA10-Foldon-Ferritin encoding sequence. In FIG. 2, PCR amplification products from positive clones are analyzed by gel electrophoresis in 1% agarose gel. A pair of forward and reverse primers are used for the amplification, namely SEQ ID NO: 8 and SEQ ID NO: 9. The expected length of the PCR product is 1,766 bp, in which the corresponding band on the gel from the lane loaded with the PCR product is between 1,650 bp and 2,000 bp with respect to the DNA marker next to the lane of the PCR product. The result indicates that the expression vector, pTRKH3, containing the DNA insert of SEQ ID NO: 1 comprising said modified OFP encoding sequence, modified influenza HA stem fragment encoding sequence and ferritin protein encoding sequence has high transformation efficiency. Positive clones so screened are subject to further confirmation and studies.

Figure 3:
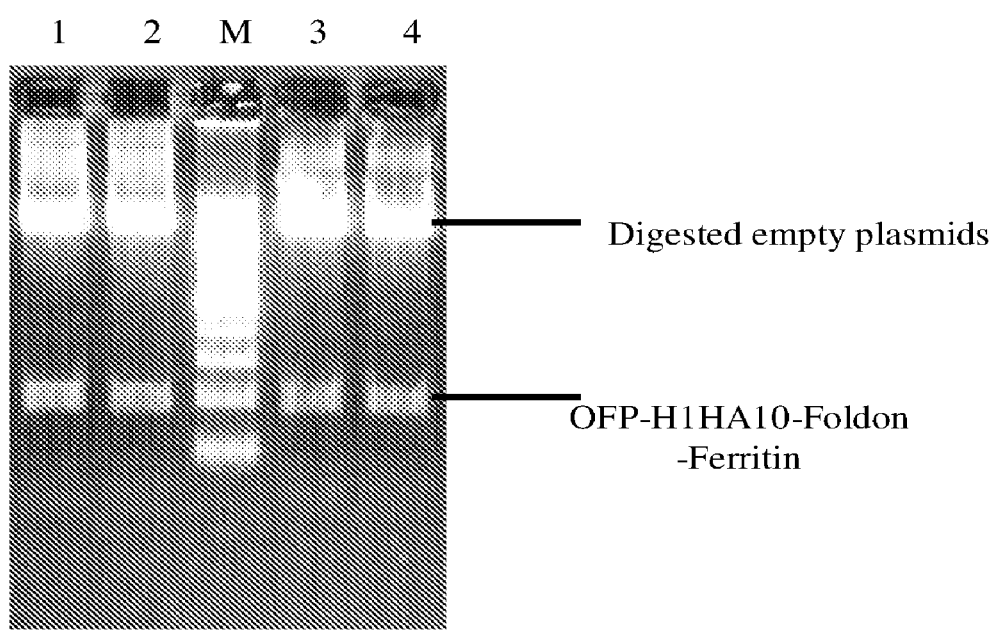
FIG. 3 shows the result of an agarose gel analysis of restriction enzyme digested cloned plasmid isolated from transformed *Lactobacillus casei* clones according to an embodiment of the present invention: (M) DNA marker; (1-4) digested cloned plasmid from *Lactobacillus casei* transformed clones.

The DNA encoding sequence of influenza hemagglutinin stem fragment (H1HA10-Foldon) is isolated from the expression vector extracted from the transformed positive clones confirmed in FIG. 2. Under double-digestion by using two specific restriction enzymes (KpnI and AgeI), the digested expression vector samples extracted from the positive clones are analyzed by agarose gel (1%) electrophoresis. FIG. 3 shows that there are two distinct bands in four samples, and it is confirmed that the expression vector used in this example is successfully transformed inside the host bacteria.

Example 2—Expression of Recombinant Protein Comprising Influenza HA Stem Fragment The positive transformed *Lactobacillus casei* clones from Example 1 which are successfully selected are capable of expressing the influenza hemagglutinin stem-fragment. To further confirm that the corresponding target fragment is expressed in the transformed *Lactobacillus casei*, Western blot is performed to assess the expression efficiency of the hemagglutinin stem fragment inside the transformed *Lactobacillus casei*. Positive clones are cultured in MRS broth supplemented with 100 μg/ml erythromycine at 37° C. with shaking at 250 rpm in anaerobic conditions for 72 hours.

Figure 4:
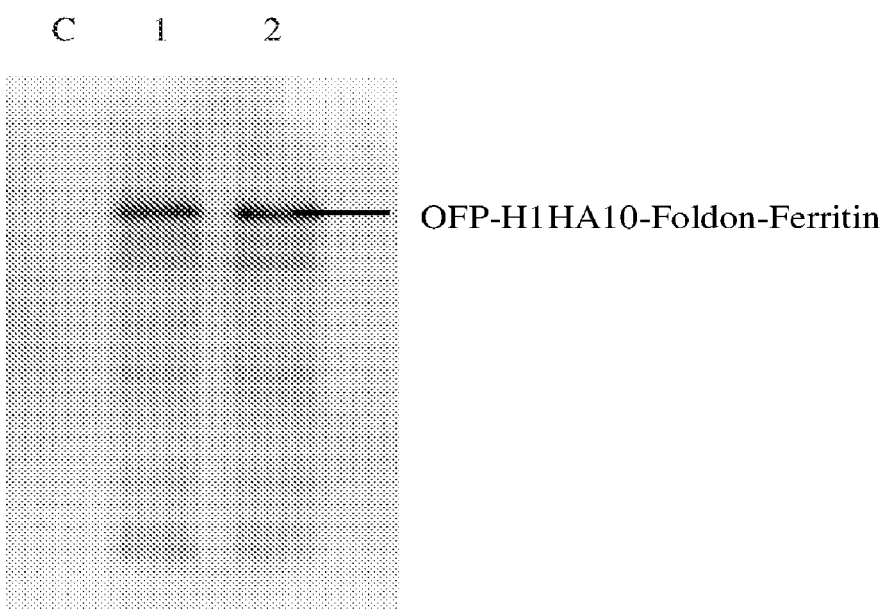
FIG. 4 shows the result of Western blot analysis of influenza hemagglutinin stem fragment-containing recombinant protein (OFP-HIHA10-Foldon-Ferritin) extracted from transformed *Lactobacillus casei* according to an embodiment of the present invention: (C) proteins extracted from wild-type *Lactobacillus casei* which serves as control: (1) and (2) proteins extracted from transformed *Lactobacillus casei*.
Figure 5:
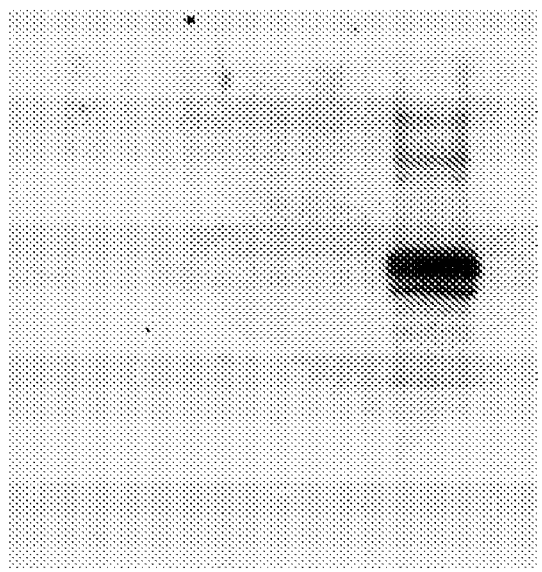
FIG. 5 shows the result of Western blot analysis of mouse serum two weeks after oral administration of the transformed *Lactobacillus casei*: (1) PBS only; (2) wild-type *Lactobacillus casei* ($1 \times 10^9$ cfu per mouse); and (3) the transformed *Lactobacillus casei* ($1 \times 10^9$ cfu per mouse) according to an embodiment of the present invention, respectively.
Figure 6:
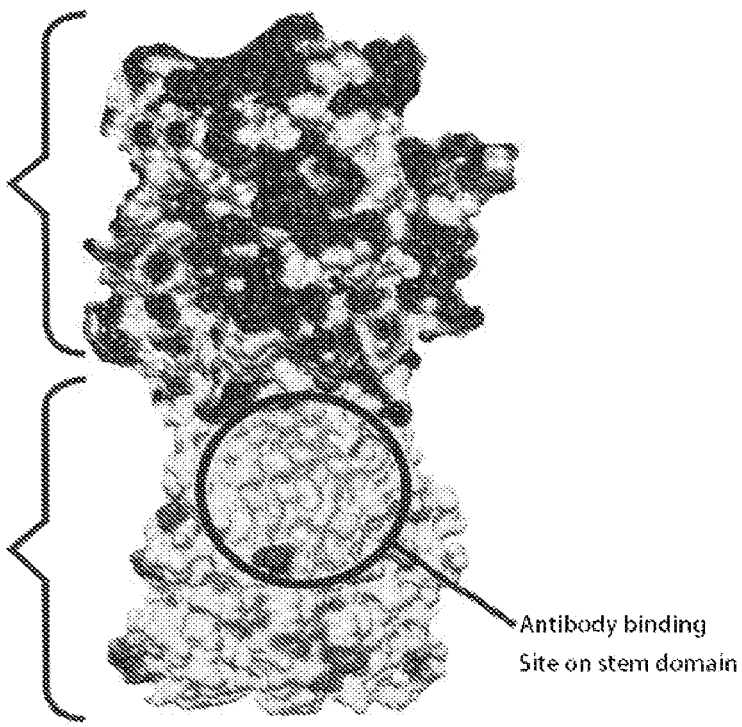
FIG. 6 is a schematic diagram showing a structure of influenza hemagglutinin.

After that, the bacterial cell suspension is collected and the collected cells are lysed to collect the cytosolic proteins. In FIG. 4, two samples are run in SDS gel followed by Western blot analysis. The significant band indicates the presence of the expression of the influenza hemagglutinin stem fragment from the transformed *Lactobacillus casei*. The amino acid sequence of the recombinant protein containing the modified OFP, modified influenza HA stem fragment (H1HA10-Foldon) and ferritin protein (OFP-H1HA10-Foldon-Ferritin) is represented by SEQ ID NO: 7.

Example 3—In Vivo Study of Immunogenicity of Recombinant Lactic Acid Bacteria BALB/c mice (6-8 weeks) (n=7) are randomly divided into three groups. Three groups are orally administered with three different formulations: PBS (Group 1), wild-type *Lactobacillus casei* resuspended in 200 μl PBS ($1\times10^9$ cfu per mouse) (Group 2); and transformed *Lactobacillus casei* confirmed in Examples 1 and 2 resuspended in 200 μl PBS ($1\times10^9$ cfu per mouse) (Group 3), respectively. Oral gavage is repeated three times (once daily, consecutive three days) on a weekly basis for two consecutive weeks. Mice are boosted twice after one week. Blood samples are collected from tail vein at week 3, 5, 7, 9 and 15 after oral gavage of three different formulations, and stored at −80° C. before testing for the presence of the antibodies interested. Also, the weight of each mouse is recorded weekly during the course of feeding period so as to monitor the health conditions of individual mouse after consumption of *Lactobacillus casei*. No loss of weight is observed and all mice are alive after the course of oral gavage as described hereinbefore.

The confirmed positive clones of expression vector containing the encoding sequence of OFP-H1HA10-Foldon-Ferritin is transformed into DH50α for generation of antibodies. The antibodies so generated are purified using His-bind fractogel column. The purified antibodies are loaded in SDS-PAGE, probed with mouse antibody from mouse serum and detected with HRP-conjugated goat anti-mouse IgG antibody (1:1000) and visualized with ECL Western blotting substrate. After feeding mice with transformed *Lactobacillus casei*, mouse serum is collected after two weeks of oral feeding and the antibody against the influenza hemagglutinin stem fragment is detected in mouse serum whereas no corresponding antibody is detected in mice orally fed with PBS or wild-type *Lactobacillus casei*. These results suggest that mice orally fed with transformed *Lactobacillus casei* generate the corresponding antibody against hemagglutinin stem fragment.

INDUSTRIAL APPLICABILITY

The present recombinant lactic acid bacteria is useful in manufacturing into a vaccine which is safe to be orally administered into a subject such as human and other animals (e.g., livestock). The expressed recombinant protein isolated and purified from a host transformed with the expression vector containing the encoding sequence of the modified influenza hemagglutinin may be used in manufacturing of the vaccine. The vaccine is not limited to oral formulation but it can also include other forms such as injectable form, provided that it does not induce immune-rejection.

Deposition of Microorganism

Pursuant to the requirements under PCT Rule 13bis, the present modified recombinant *Lactobacillus casei* has been deposited at the following International Depositary Authority:

Name of Deposit Institute: Guangdong Microbial Culture Collection Center (GDMCC), Guangdong Institute of Microbiology Address of Deposit Institute: No. 59 Building, 100 Xianlie Central Road, Guangzhou 510070, China Date of Deposit: 18 Nov. 2016

GDMCC No.: 60113

What is claimed is:

1. An oral formulation for targeting a variety of influenza viruses causing influenza and treating said influenza in a subject in need thereof comprising a recombinant lactic acid bacterial cell transformed with an expression vector containing an encoding sequence for encoding a fusion protein comprising a fluorescent protein, a stem domain of influenza hemagglutinin, a ferritin protein and two linkers, and a pharmaceutically acceptable carrier, wherein the encoding sequence encoding the fluorescent protein and encoding the stem domain of influenza hemagglutinin have been codon optimized for expression in lactic acid bacteria and wherein in the fusion protein said two linkers link the stem domain of influenza hemagglutinin, the fluorescent protein, and the ferritin protein.

2. The oral formulation of claim 1, wherein said fluorescent protein is orange fluorescent protein originated from *Cerianthus* sp.

3. The oral formulation of claim 1, wherein said stem domain of influenza hemagglutinin comprises a H1HA10 stem fragment and T4 bacteriophage fibritin foldon.

4. The oral formulation of claim 1, wherein said ferritin protein is originated from *Helicobacter pylori*.

5. The oral formulation of claim 1, wherein said encoding sequence is one of the SEQ ID NOs: 1-6.

6. The oral formulation of claim 5, wherein said encoding sequence is SEQ ID NO: 1.

7. The oral formulation of claim 1, wherein said lactic acid bacterial cell is from the strains comprising *Lactobacillus* sp. and *Lactococcus* sp.

8. The oral formulation of claim 1, wherein said expression vector is an expression vector that is for expressing protein in gram-positive bacterial host cells.

9. The oral formulation of claim 1, wherein said lactic acid bacterial cell is from *Lactobacillus casei*.

10. The oral formulation of claim 1, wherein said expression vector is pTRKH3.

11. The oral formulation of claim 1, wherein the encoding sequence for the first linker is positioned between the encoding sequence of the fluorescent protein and stem domain of influenza hemagglutinin, and the encoding sequence for the second linker is positioned between the encoding sequence of the stem domain of influenza hemagglutinin and ferritin protein.

12. The oral formulation of claim 11, wherein said first linker comprises an Factor Xa (Xa) protease encoding sequence, a restriction site of KpnI, and a poly-His encoding sequence.

13. The oral formulation of claim 11, wherein said second linker comprises Tobacco Etch Virus (TEV) protease encoding sequence and a restriction site of AgeI.

14. A method for treating influenza caused by a variety of influenza viruses comprising orally administering the oral formulation of claim 1 to a subject in need thereof.

15. The method of claim 14, wherein said oral formulation is orally administered to said subject once daily for three consecutive days on weekly basis and for two consecutive weeks.

16. The oral formulation of claim 1, wherein said variety of influenza viruses comprises H1, H3, and H5.

17. The oral formulation of claim 1, wherein said oral formulation is formulated into a form comprising powder, pills, capsules, liquid, and tablets.

* * * * *

SEQUENCE LISTING

```
<160> NUMBER OF SEQ ID NOS: 9

<210> SEQ ID NO 1
<211> LENGTH: 1749
<212> TYPE: DNA
<213> ORGANISM: Artificial Sequence
<220> FEATURE:
<223> OTHER INFORMATION: Modified OFP and H1HA10 stem domain plus
      Ferritin Proteins

<400> SEQUENCE: 1
atgaacctga gcaagaatgt tagcgttagc gtttatatga aaggcaatgt taataatcac     60
gaatttgaat atgacggcga aggcggtggc gatccatata ccggtaagta tagtatgaag    120
atgactttgc gtggtcaaaa tagtttgcca ttcagttatg atattatcac cacagccttc    180
caatatggct ttcgcgtttt tacaaaatat ccagaaggta tcgttgatta tttcaaggat    240
tcattgccag atgcttttca atggaatcgt cgcattgttt ttgaagatgg tggcgttttg    300
aatatgagtt cagatattac atataaggat aacgttttac atggcgatgt taaagctgaa    360
ggtgttaatt ttccaccaaa tggcccagtt atgaagaacg aaatcgttat ggaagaacca    420
actgaagaaa cctttacacc aaaaaatggc gttttggttg gtttctgtcc aaaagcatat    480
ttgttgaagg atggcagtta ttattatggt aacatgacta ccttctatcg tagtaaaaaa    540
```

```
tcaggccaag caccaccagg ttatcatttc gttaagcatc gcttggttaa gactaacgtt    600
ggtcatggtt tcaagactgt tgaacaaacc gaatatgcca cagctcatgt tagtgatttg    660
ccaaaaattg aaggccgtgg tacccatcat catcatcatc atgataccgt tgatacagtt    720
ttagaaaaga atgttactgt tacccattca gttaacttat tggaagatag tcatggttca    780
gcaaatagtt cattaccata tcaaaacaca catccaacaa ctaatggcga agtccaaaa     840 tatgttcgtt cagcaaaatt gcgcatggtt acaggtttac gcaatggcag tgcaggttca    900
gccactcaaa atgccattaa tggcattact aacaaggtta acaccgttat cgaaaagatg    960
aatattcaag atacagccac tggcaaggaa tttaacaagg atgaaaaacg tatggaaaac   1020
ttgaacaaga aagttgatga tggcttttta gatatttgga cctataacgc agaattattg   1080
gttttattgg aaaacgaacg caccttggat gcccatgata gtcaaggcac aggtggcggt   1140
tatattccag aagctccacg tgatggccaa gcctatgttc gcaaagatgg tgaatgggtt   1200
ttgttaagta ccttttttaga aaacttgtat tttcaaggca ccggcatgtt gtcaaaggat   1260
attatcaaat tgttgaatga acaagttaat aaagaaatga atagttcaaa tttgtatatg   1320
agtatgagtt catggtgcta tacacattca ttagatggcg ctggtttatt tttgtttgat   1380
catgctgcag aagaatatga acatgctaaa aaattaatca ttttcttaaa cgaaaataat   1440
gttccagttc aattgaccag tatttcagcc ccagaacata agttcgaagg tttgacacaa   1500 attttttcaaa aagcctatga acatgaacaa catatcagtg aatcaatcaa caacattgtt   1560
gatcatgcca tcaagtcaaa ggatcatgct accttcaact ttttacaatg gtatgttgca   1620
gaacaacatg aagaagaagt tttatttaaa gatattttgg ataaaattga attaattggc   1680
aatgaaaatc acggtttgta tttagcggac cagtatgtca agggtattgc gaagtcacga   1740
aagtcttaa                                                            1749

<210> SEQ ID NO 2
<211> LENGTH: 1749
<212> TYPE: DNA
<213> ORGANISM: Artificial Sequence
<220> FEATURE:
<223> OTHER INFORMATION: OFP-Ferritin-H1HA10-Foldon

<400> SEQUENCE: 2 atgaaccctga g

```
gctgcagaag aatatgaaca tgctaaaaaa ttaatcattt tcttaaacga aaataatgtt    900
ccagttcaat tgaccagtat ttcagcccca gaacataagt tcgaaggttt gacacaaatt    960
tttcaaaaag cctatgaaca tgaacaacat atcagtgaat caatcaacaa cattgttgat   1020
catgccatca agtcaaagga tcatgctacc ttcaactttt tacaatggta tgttgcagaa   1080
caacatgaag aagaagttttt atttaaagat attttggata aaattgaatt aattggcaat   1140
gaaaatcacg gtttgtattt agcggaccag tatgtcaagg gtattgcgaa gtcacgaaag   1200
tctgaaaact tgtattttca aggcaccggc gataccgttg atacagtttt agaaaagaat   1260
gttactgtta cccattcagt taacttattg gaagatagtc atggttcagc aaatagttca   1320
ttaccatatc aaaacacaca tccaacaact aatggcgaaa gtccaaaata tgttcgttca   1380
gcaaaattgc gcatggttac aggtttacgg aatggcagtg caggttcagc cactcaaaat   1440
gccattaatg gcattactaa caaggttaac accgttatcg aaaagatgaa tattcaagat   1500
acagccactg gcaaggaatt taacaaggat gaaaaacgta tggaaaactt gaacaagaaa   1560
gttgatgatg cttttttaga tatttggacc tataacgcag aattattggt tttattggaa   1620
aacgaacgca ccttggatgc ccatgatagt caaggcacag gtggcggtta tattccagaa   1680
gctccacgtg atggccaagc ctatgttcgc aaagatggtg aatgggtttt gttaagtacc   1740
tttttataa                                                          1749

<210> SEQ ID NO 3
<211> LENGTH: 1752
<212> TYPE: DNA
<213> ORGANISM: Artificial Sequence
<220> FEATURE:
<223> OTHER INFORMATION: H1HA10-Foldon-OFP-Ferritin

<400> SEQUENCE: 3
atggataccg ttgatacagt tttagaaaag aatgttactg ttacccattc agttaactta     60
ttggaagata gtcatggttc agcaaatagt tcattaccat atcaaaacac acatccaaca    120
actaatggcg aaagtccaaa atatgttcgt tcagcaaaat tgcgcatggt tacaggttta    180
cgcaatggca gtgcaggttc agccactcaa atgccattaa tggcattact aacaaggtt    240 aacaccgtta tcgaaaagat gaatattcaa gatacagcca ctggcaagga atttaacaag    300
gatgaaaaac gtatggaaaa cttgaacaag aaagttgatg atgcttttttt agatatttgg    360 acctataacg cagaattatt ggttttattg gaaaacgaac gcaccttgga tgcccatgat    420
agtcaaggca caggtggcgg ttatattcca gaagctccac gtgatggcca agcctatgtt    480
cgcaaagatg gtgaatgggt tttgttaagt accttttttaa ttgaaggccg tggtacccat    540
catcatcatc atcatatgaa cctgagcaag atgttagcg ttagcgttta tatgaaaggc    600
aatgttaata tcacgaatt tgaatatgac ggcgaaggcg gtggcgatcc atataccggt    660
aagtatagta tgaagatgac tttgcgtggt caaaatagtt tgccattcag ttatgatatt    720
atcaccacag ccttccaata tggctttcgc gtttttacaa aatatccaga aggtatcgtt    780
gattatttca aggattcatt gccagatgct tttcaatgga atcgtcgcat tgttttttgaa    840 gatggtggcg ttttgaatat gagttcgat attacatata aggataacgt tttacatggc    900
gatgttaaag ctgaaggtgt taatttttcca ccaaatggcc cagttatgaa gaacgaaatc    960
gttatggaag aaccaactga agaaaccttt acaccaaaaa atggcgtttt ggttggtttc   1020
tgtccaaaag catatttgtt gaaggatggc agttattatt atggtaacat gactaccttc   1080
```

-continued tatcgtagta aaaaatcagg ccaagcacca ccaggttatc atttcgttaa gcatcgcttg 1140
gttaagacta acgttggtca tggtttcaag actgttgaac aaaccgaata tgccacagct 1200
catgttagtg atttgccaaa agaaaacttg tattttcaag gcaccggcat gttgtcaaag 1260
gatattatca aattgttgaa tgaacaagtt aataaagaaa tgaatagttc aaatttgtat 1320
atgagtatga gttcatggtg ctatacacat tcattagatg gcgctggttt atttttgttt 1380
gatcatgctg cagaagaata tgaacatgct aaaaaattaa tcatttttctt aaacgaaaat 1440 aatgttccag ttcaattgac cagtatttca gccccagaac ataagttcga aggtttgaca 1500
caaatttttc aaaaagccta tgaacatgaa caacatatca gtgaatcaat caacaacatt 1560
gttgatcatg ccatcaagtc aaaggatcat gctaccttca actttttaca atggtatgtt 1620
gcagaacaac atgaagaaga agttttattt aaagatattt tggataaaat tgaattaatt 1680
ggcaatgaaa atcacggttt gtatttagcg gaccagtatg tcaagggtat tgcgaagtca 1740
cgaaagtctt aa 1752

<210> SEQ ID NO 4
<211> LENGTH: 1752
<212> TYPE: DNA
<213> ORGANISM: Artificial Sequence
<220> FEATURE:
<223> OTHER INFORMATION: H1HA10-Foldon-Ferritin-OFP

<400> SEQUENCE: 4
atggataccg ttgatacagt tttagaaaag aatgttactg ttacccattc agttaactta 60
ttggaagata gtcatggttc agcaaatagt tcattaccat atcaaaacac acatccaaca 120
actaatggcg aaagtccaaa atatgttcgt tcagcaaaat tgcgcatggt tacaggttta 180
cgcaatggca gtgcaggttc agccactcaa aatgccatta atggcattac taacaaggtt 240
aacaccgtta tcgaaaagat gaatattcaa gatacagcca ctggcaagga atttaacaag 300
gatgaaaaac gtatggaaaa cttgaacaag aaagttgatg atggcttttt agatatttgg 360
acctataacg cagaattatt ggttttattg gaaaacgaac gcaccttgga tgcccatgat 420
agtcaaggca caggtggcgg ttatattcca gaagctccac gtgatggcca agcctatgtt 480
cgcaaagatg gtgaatgggt tttgttaagt accttttaa ttgaaggccg tggtacccat 540
catcatcatc atcatatgtt gtcaaaggat attatcaaat tgttgaatga acaagttaat 600
aaagaaatga atagttcaaa tttgtatatg agtatgagtt catggtgcta tacacattca 660
ttagatggcg ctggtttatt tttgtttgat catgctgcag aagaatatga acatgctaaa 720
aaattaatca ttttcttaaa cgaaaataat gttccagttc aattgaccag tatttcagcc 780
ccagaacata agttcgaagg tttgacacaa atttttcaaa aagcctatga acatgaacaa 840
catatcagtg aatcaatcaa caacattgtt gatcatgcca tcaagtcaaa ggatcatgct 900
accttcaact ttttacaatg gtatgttgca gaacaacatg aagaagaagt tttatttaaa 960
gatattttgg ataaaattga attaattggc aatgaaaatc acggtttgta tttagcggac 1020
cagtatgtca agggtattgc gaagtcacga aagtctgaaa acttgtattt tcaaggcacc 1080
ggcatgaacc tgagcaagaa tgttagcgtt agcgtttata tgaaaggcaa tgttaataat 1140
cacgaatttg aatatgacgg cgaaggcggt ggcgatccat ataccggtaa gtatagtatg 1200
aagatgactt tgcgtggtca aaatagtttg ccattcagtt atgatattat caccacagcc 1260
ttccaatatg gctttcgcgt ttttacaaaa tatccagaag gtatcgttga ttatttcaag 1320
gattcattgc cagatgcttt tcaatggaat cgtcgcattg tttttgaaga tggtggcgtt 1380

| | |
|---|---|
| ttgaatatga gttcagatat tacatataag gataacgttt tacatggcga tgttaaagct | 1440 |
| gaaggtgtta attttccacc aaatggccca gttatgaaga cgaaatcgt tatggaagaa | 1500 |
| ccaactgaag aaacctttac accaaaaaat ggcgttttgg ttggtttctg tccaaaagca | 1560 |
| tatttgttga aggatggcag ttattattat ggtaacatga ctaccttcta tcgtagtaaa | 1620 |
| aaatcaggcc aagcaccacc aggttatcat ttcgttaagc atcgcttggt taagactaac | 1680 |
| gttggtcatg gtttcaagac tgttgaacaa accgaatatg ccacagctca tgttagtgat | 1740 |
| ttgccaaaat aa | 1752 |

<210> SEQ ID NO 5
<211> LENGTH: 1749
<212> TYPE: DNA
<213> ORGANISM: Artificial Sequence
<220> FEATURE:
<223> OTHER INFORMATION: Ferritin-OFP-H1HA10-Foldon

<400> SEQUENCE: 5

| | |
|---|---|
| atgttgtcaa aggatattat caaattgttg aatgaacaag ttaataaaga atgaatagt | 60 |
| tcaaatttgt atatgagtat gagttcatgg tgctatacac attcattaga tggcgctggt | 120 |
| ttatttttgt ttgatcatgc tgcagaagaa tatgaacatg ctaaaaaatt aatcattttc | 180 |
| ttaaacgaaa ataatgttcc agttcaattg accagtattt cagccccaga acataagttc | 240 |
| gaaggtttga cacaaatttt tcaaaaagcc tatgaacatg aacaacatat cagtgaatca | 300 |
| atcaacaaca ttgttgatca tgccatcaag tcaaaggatc atgctacctt caacttttta | 360 |
| caatggtatg ttgcagaaca acatgaagaa gaagtttttat ttaaagatat tttggataaa | 420 |
| attgaattaa ttggcaatga aaatcacggt ttgtatttag cggaccagta tgtcaagggt | 480 |
| attgcgaagt cacgaaagtc tattgaaggc cgtggtaccc atcatcatca tcatcatatg | 540 |
| aacctgagca agaatgttag cgttagcgtt tatatgaaag gcaatgttaa taatcacgaa | 600 |
| tttgaatatg acggcgaagg cggtggcgat ccatataccg gtaagtatag tatgaagatg | 660 |
| actttgcgtg gtcaaaatag tttgccattc agttatgata ttatcaccac agccttccaa | 720 |
| tatggctttc gcgtttttac aaaatatcca gaaggtatcg ttgattattt caaggattca | 780 |
| ttgccagatg cttttcaatg gaatcgtcgc attgttttg aagatggtgg cgttttgaat | 840 |
| atgagttcag atattacata taaggataac gttttacatg gcgatgttaa agctgaaggt | 900 |
| gttaattttc caccaaatgg cccagttatg aagaacgaaa tcgttatgga agaaccaact | 960 |
| gaagaaacct ttacaccaaa aaatggcgtt tggttggt tctgtccaaa agcatatttg | 1020 |
| ttgaaggatg gcagttatta ttatggtaac atgactacct tctatcgtag taaaaaatca | 1080 |
| ggccaagcac caccaggtta tcatttcgtt aagcatcgct tggttaagac taacgttggt | 1140 |
| catggtttca agactgttga acaaaccgaa tatgccacag ctcatgttag tgatttgcca | 1200 |
| aaagaaaact gtatttcca aggcaccggc gataccgttg atacagtttt agaaaagaat | 1260 |
| gttactgtta cccattcagt taacttattg gaagatagtc atggttcagc aaatagttca | 1320 |
| ttaccatatc aaaacacaca tccaacaact aatggcgaaa gtccaaaata tgttcgttca | 1380 |
| gcaaaattgc gcatggttac aggtttacgc aatggcagtc aggttcagc cactcaaaat | 1440 |
| gccattaatg gcattactaa caaggttaac accgttatcg aaaagatgaa tattcaagat | 1500 |
| acagccactg gcaaggaatt taacaaggat gaaaaacgta tggaaaactt gaacaagaaa | 1560 |
| gttgatgatg gcttttttaga tatttggacc tataacgcag aattattggt tttattggaa | 1620 |

```
aacgaacgca ccttggatgc ccatgatagt caaggcacag gtggcggtta tattccagaa    1680
gctccacgtg atggccaagc ctatgttcgc aaagatggtg aatgggtttt gttaagtacc    1740
tttttataa                                                            1749

<210> SEQ ID NO 6
<211> LENGTH: 1749
<212> TYPE: DNA
<213> ORGANISM: Artificial Sequence
<220> FEATURE:
<223> OTHER INFORMATION: Ferritin-H1HA10-Foldon-OFP

<400> SEQUENCE: 6
atgttgtcaa aggatattat caaattgttg aatgaacaag ttaataaaga atgaatagt       60 tcaaatttgt atatgagtat gagttcatgg tgctatacac attcattaga tggcgctggt     120 ttattttttgt ttgatcatgc tgcagaagaa tatgaacatg ctaaaaaatt aatcattttc    180
ttaaacgaaa ataatgttcc agttcaattg accagtattt cagccccaga acataagttc    240
gaaggtttga cacaaatttt tcaaaaagcc tatgaacatg acaacatat cagtgaatca     300 atcaacaaca ttgttgatca tgccatcaag tcaaggatc atgctaccct caacttttta     360
caatggtatg ttgcagaaca acatgaagaa gaagttttat ttaaagatat tttggataaa    420
attgaattaa ttggcaatga aaatcacggt ttgtatttag cggaccagta tgtcaagggt    480
attgcgaagt cacgaaagtc tattgaaggc cgtggtaccc atcatcatca tcatcatgat    540
accgttgata cagttttaga aaagaatgtt actgttaccc attcagttaa cttattggaa    600
gatagtcatg gttcagcaaa tagttcatta ccatatcaaa acacacatcc aacaactaat    660
ggcgaaagtc caaaatatgt tcgttcagca aaattgcgca tggttacagg tttacgcaat    720
ggcagtgcag gttcagccac tcaaaatgcc attaatggca ttactaacaa ggttaacacc    780
gttatcgaaa agatgaatat tcaagataca gccactggca aggaattta caaggatgaa    840 aaacgtatgg aaaacttgaa caagaaagtt gatgatggct tttagatat ttggacctat     900 aacgcagaat tattggtttt attggaaaac gaacgcacct ggatgccca tgatagtcaa     960 ggcacaggtg gcggttatat tccagaagct ccacgtgatg ccaagccta tgttcgcaaa    1020 gatggtgaat gggttttgtt aagtaccttt ttagaaaact tgtattttca aggcaccggc    1080
atgaacctga gcaagaatgt tagcgttagc gtttatatga aaggcaatgt taataatcac    1140
gaatttgaat atgacggcga aggcggtggc gatccatata ccggtaagta tagtatgaag    1200
atgactttgc gtggtcaaaa tagttttgcca ttcagttatg atattatcac cacagccttc    1260
caatatggct ttcgcgtttt tacaaaatat ccagaaggta tcgttgatta tttcaaggat    1320
tcattgccag atgctttcca atggaatcgt cgcattgttt ttgaagatgg tggcgttttg    1380
aatatgagtt cagatattac atataaggat aacgttttac atggcgatgt taaagctgaa    1440
ggtgttaatt ttccaccaaa tggcccagtt atgaagaacg aaatcgttat ggaagaacca    1500
actgaagaaa ccttttacacc aaaaaatggc gttttggttg gtttctgtcc aaaagcatat    1560 tgttgaagg atggcagtta ttattatggt aacatgacta ccttctatcg tagtaaaaaa    1620
tcaggccaag caccaccagg ttatcatttc gttaagcatc gcttggttaa gactaacgtt    1680
ggtcatggtt tcaagactgt tgaacaaacc gaatatgcca cagctcatgt tagtgatttg    1740
ccaaaataa                                                            1749

<210> SEQ ID NO 7
<211> LENGTH: 582
```

<212> TYPE: PRT
<213> ORGANISM: Artificial Sequence
<220> FEATURE:
<223> OTHER INFORMATION: Modified OFP and H1HA10 Stem Domain Plus
      Ferritin Protein

<400> SEQUENCE: 7

```
Met Asn Leu Ser Lys Asn Val Ser Val Ser Val Tyr Met Lys Gly Asn
1               5                   10                  15

Val Asn Asn His Glu Phe Glu Tyr Asp Gly Glu Gly Gly Gly Asp Pro
            20                  25                  30

Tyr Thr Gly Lys Tyr Ser Met Lys Met Thr Leu Arg Gly Gln Asn Ser
        35                  40                  45

Leu Pro Phe Ser Tyr Asp Ile Ile Thr Thr Ala Phe Gln Tyr Gly Phe
    50                  55                  60

Arg Val Phe Thr Lys Tyr Pro Glu Gly Ile Val Asp Tyr Phe Lys Asp
65                  70                  75                  80

Ser Leu Pro Asp Ala Phe Gln Trp Asn Arg Arg Ile Val Phe Glu Asp
                85                  90                  95

Gly Gly Val Leu Asn Met Ser Ser Asp Ile Thr Tyr Lys Asp Asn Val
            100                 105                 110

Leu His Gly Asp Val Lys Ala Glu Gly Val Asn Phe Pro Pro Asn Gly
        115                 120                 125

Pro Val Met Lys Asn Glu Ile Val Met Glu Glu Pro Thr Glu Glu Thr
    130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys Ile Glu
    210                 215                 220

Gly Arg Gly Thr His His His His His His Asp Thr Val Asp Thr Val
225                 230                 235                 240

Leu Glu Lys Asn Val Thr Val Thr His Ser Val Asn Leu Leu Glu Asp
                245                 250                 255

Ser His Gly Ser Ala Asn Ser Ser Leu Pro Tyr Gln Asn Thr His Pro
            260                 265                 270

Thr Thr Asn Gly Glu Ser Pro Lys Tyr Val Arg Ser Ala Lys Leu Arg
        275                 280                 285

Met Val Thr Gly Leu Arg Asn Gly Ser Ala Gly Ser Ala Thr Gln Asn
    290                 295                 300

Ala Ile Asn Gly Ile Thr Asn Lys Val Asn Thr Val Ile Glu Lys Met
305                 310                 315                 320

Asn Ile Gln Asp Thr Ala Thr Gly Lys Glu Phe Asn Lys Asp Glu Lys
                325                 330                 335

Arg Met Glu Asn Leu Asn Lys Lys Val Asp Asp Gly Phe Leu Asp Ile
            340                 345                 350

Trp Thr Tyr Asn Ala Glu Leu Leu Val Leu Leu Glu Asn Glu Arg Thr
        355                 360                 365

Leu Asp Ala His Asp Ser Gln Gly Thr Gly Gly Gly Tyr Ile Pro Glu
    370                 375                 380
```

```
Ala Pro Arg Asp Gly Gln Ala Tyr Val Arg Lys Asp Gly Glu Trp Val
385                 390                 395                 400

Leu Leu Ser Thr Phe Leu Glu Asn Leu Tyr Phe Gln Gly Thr Gly Met
                405                 410                 415

Leu Ser Lys Asp Ile Ile Lys Leu Leu Asn Glu Gln Val Asn Lys Glu
            420                 425                 430

Met Asn Ser Ser Asn Leu Tyr Met Ser Met Ser Ser Trp Cys Tyr Thr
            435                 440                 445

His Ser Leu Asp Gly Ala Gly Leu Phe Leu Phe Asp His Ala Ala Glu
        450                 455                 460

Glu Tyr Glu His Ala Lys Lys Leu Ile Ile Phe Leu Asn Glu Asn Asn
465                 470                 475                 480

Val Pro Val Gln Leu Thr Ser Ile Ser Ala Pro Glu His Lys Phe Glu
                485                 490                 495

Gly Leu Thr Gln Ile Phe Gln Lys Ala Tyr Glu His Glu Gln His Ile
                500                 505                 510

Ser Glu Ser Ile Asn Asn Ile Val Asp His Ala Ile Lys Ser Lys Asp
            515                 520                 525

His Ala Thr Phe Asn Phe Leu Gln Trp Tyr Val Ala Glu Gln His Glu
            530                 535                 540

Glu Glu Val Leu Phe Lys Asp Ile Leu Asp Lys Ile Glu Leu Ile Gly
545                 550                 555                 560

Asn Glu Asn His Gly Leu Tyr Leu Ala Asp Gln Tyr Val Lys Gly Ile
                565                 570                 575

Ala Lys Ser Arg Lys Ser
            580

<210> SEQ ID NO 8
<211> LENGTH: 18
<212> TYPE: DNA
<213> ORGANISM: Artificial Sequence
<220> FEATURE:
<223> OTHER INFORMATION: Forward Primer for PCR Amplification

<400> SEQUENCE: 8
atgaacctga gcaagaat                                                 18

<210> SEQ ID NO 9
<211> LENGTH: 20
<212> TYPE: DNA
<213> ORGANISM: Artificial Sequence
<220> FEATURE:
<223> OTHER INFORMATION: Reverse Primer for PCR Amplification

<400> SEQUENCE: 9 ttaagactttt cgtgacttcg                                              20
```